United States Patent [19]

Leonard

[11] Patent Number: 5,360,407
[45] Date of Patent: Nov. 1, 1994

[54] IMPLANTABLE DUAL ACCESS PORT WITH TACTILE RIDGE FOR POSITION SENSING

[75] Inventor: Arnie Leonard, Minneapolis, Minn.; Daniel C. Wadsworth, Jr., Sandy, Utah

[73] Assignee: C. R. Bard, Inc., Murray Hill, N.J.

[21] Appl. No.: 753,179

[22] Filed: Aug. 29, 1991

[51] Int. Cl.$^5$ .............................................. A61M 5/32
[52] U.S. Cl. ................................. 604/175; 604/93; 604/116
[58] Field of Search ................... 604/80, 116, 175, 43, 604/280, 93, 131–133, 140, 905, 256, 244

[56] References Cited

U.S. PATENT DOCUMENTS

| | | | |
|---|---|---|---|
| 3,461,869 | 8/1969 | Hargest | 128/214 |
| 3,768,102 | 10/1973 | Kwan-Gett et al. | 3/1 |
| 3,826,257 | 7/1974 | Buselmeier | 128/214 R |
| 4,122,858 | 10/1978 | Schiff | 128/348 |
| 4,133,312 | 1/1979 | Burd | 128/214 R |
| 4,306,545 | 12/1981 | Ivan et al. | 128/1 R |
| 4,344,435 | 8/1982 | Aubin | 128/350 R |
| 4,405,305 | 9/1983 | Stephen et al. | 604/49 |
| 4,405,320 | 9/1983 | Cracauer et al. | 604/175 |
| 4,673,394 | 6/1987 | Fenton, Jr. et al. | 604/175 |
| 4,681,560 | 7/1987 | Schulte et al. | 604/9 |
| 4,685,905 | 8/1987 | Jeanneret nee Aab | 604/247 |
| 4,692,146 | 9/1987 | Hilger | 604/93 |
| 4,693,707 | 9/1987 | Dye | 604/111 |
| 4,695,273 | 9/1987 | Brown | 604/173 |
| 4,704,103 | 11/1987 | Stöber et al. | 604/175 |
| 4,710,174 | 12/1987 | Moden et al. | 604/175 |
| 4,762,517 | 8/1988 | McIntyre et al. | 604/175 |
| 4,772,270 | 9/1988 | Wiita et al. | 604/175 |
| 4,772,276 | 9/1988 | Wiita et al. | 604/283 |
| 4,781,693 | 11/1988 | Martinez et al. | 604/175 |
| 4,822,341 | 4/1989 | Colone | 604/175 |
| 4,892,518 | 1/1990 | Cupp et al. | 604/93 |
| 4,905,682 | 3/1990 | Khayat | 604/175 |
| 4,911,696 | 3/1990 | Miyasaka et al. | 604/244 |
| 4,915,690 | 4/1990 | Cone et al. | 604/93 |
| 4,929,236 | 5/1990 | Sampson | 604/175 |
| 4,955,861 | 9/1990 | Enegren et al. | 604/141 |
| 4,963,133 | 10/1990 | Whipple | 604/283 |

FOREIGN PATENT DOCUMENTS

| | | |
|---|---|---|
| 0134745 | 3/1985 | European Pat. Off. |
| 0157906 | 10/1985 | European Pat. Off. |
| 0343910 | 11/1989 | European Pat. Off. |
| 0366814 | 5/1990 | European Pat. Off. |
| WO90/14118 | 11/1990 | WIPO |

Primary Examiner—C. Fred Rosenbaum
Assistant Examiner—Mark Bockelman
Attorney, Agent, or Firm—Workman, Nydegger & Jensen

[57] ABSTRACT

The invention comprises an infusion device for infusing fluids to a patient having a plurality of, preferably two, enclosed open cavities, equipped with self-sealing septums. The device comprises a housing having a base, a cap, and a dual-port stem exiting the base and communicating with the open cavities. The cap comprises a tactile raised locating ridge positioned between, and adjacent to, the septums or other self-sealing means so configured that a doctor can simultaneously determine where each septum is located as soon as he locates the single ridge. A doctor can also differentiate between each septum, and determine the location of structures associated with each septum. Furthermore, the ridge is so configured that it does not enclose an area of tissue of the patient, thereby precluding the problem of necrosis.

38 Claims, 4 Drawing Sheets

IMPLANTABLE DUAL ACCESS PORT WITH TACTILE RIDGE FOR POSITION SENSING

BACKGROUND

1. Field of the Invention

The invention is in the field of implantable infusion devices having a plurality of penetrable self-sealing septums leading to a plurality of open cavities which are implanted under the skin of a patient, whereby medications or other fluids may be introduced into the device by means of a hypodermic needle or catheter for dispensing the medications to selected areas of the body.

2. The Related Technology

A variety of implantable infusion devices, also known as implantable ports, are well known in the art. These usually comprise a housing portion which is received on a base portion having an open cavity formed therein which is accessible through a reduced entry passage in the upper end of the housing portion, a penetrable sealed portion which is received in the entry passage in the housing portion, and means for one or more outlets to communicate with the open cavities for dispensing the medication to a predetermined location. The medication is dispensed from the outlets to the predetermined location by the use of a catheter element.

The implantable device is implanted under the skin of a patient, preferably together with a catheter which communicates between the open cavities and some other portion of the body, such as the venous system. The implantable device typically acts as an implantable injection cap for the direct infusion of medication or fluid. Additional quantities of medication or fluid may, thereafter, be dispensed from the open cavity subsequent to an initial injection by means of a hypodermic needle or catheter or cannula which passes through the skin of the patient and the septum into the open cavity.

Medication or fluid may be dispensed or infused to a point of application in a variety of procedures. One procedure for dispensing medication or fluid provides for a bolus infusion. The infusion of a drug by this procedure involves the injection of a drug through an insertion route created by a syringe passing through the septum through the open cavity to the point of application. Thereafter, the insertion route is flushed with saline, heparin or a combination thereof (resulting in a heparin-lock) to cleanse the insertion route and prevent infection or contamination.

Alternatively, one may continually infuse medication or fluid to a point of application. This procedure for dispensing medication or fluid involves the use of a catheter and needle, which is attached to an ambulatory-type pump or an IV bag suspended above a patient, to communicate with the insertion route defined by the implantable infusion device. The ambulatory-type pump, or IV bag, by virtue of gravity, continually feed the medication or fluid through the insertion route to the point of application.

Whereas the infusion of medication or fluid is often practiced, implantable devices may be used to withdraw fluids from a patient, such as blood. This procedure involves the use of a needle communicating with the insertion route (or, in this case, withdrawal route) to draw blood from a point in the body, usually the venous system. Blood initially withdrawn from a patient is discarded due to possible contamination, but subsequent samples are taken for testing or other uses. Thereafter, to prevent clotting, the withdrawal route is flushed as previously described.

Certain basic problems have been experienced with such devices. In order to supply medication to the open cavity, it becomes necessary to locate the septum covering the open cavity. Because the implantable device is subcutaneously placed, this is normally effected by feel. Generally, a septum on an implantable device is smooth and relatively flat and, therefore, due to the subcutaneous placement of the implantable device, most individuals are incapable of identifying the location of the septum tactilely.

Whereas the use of a type of tactile locating device for the septum has been attempted in the art, this tactile locating device has not proven to be particularly useful in the art. This type of tactile locating device involves the placement of a raised circular ring about the entire outer perimeter of a septum. Such a construction has raised concern to some individuals.

Doctors are concerned that necrosis may develop in response to such an enclosed circular ring about the septum. They fear that the enclosed area encircled by the circular ring may result in the blood supply to the enclosed area becoming adversely affected, thus allowing necrosis to develop. This not only adversely affects the localized tissue, but interferes with the infusion or withdrawal of medication or fluid from the implantable infusion device.

Even if an individual could determine the location of the septum by touch, a further problem is presented. That portion of the septum that can be positively identified is usually only the perimeter of the rubberized septum, differentiated at its perimeter by the rigid surrounding housing portion. Most individuals will attempt to access the open cavity at a point next to the septum perimeter to ensure the cavity is accessed and prevent their straying away from the septum area.

The fact that individuals attempt to access the septum at its perimeter is detrimental in that the puncture life of the septum in that area is reduced. Normally, if one could identify the septum in its entirety, one would not concentrate the area susceptive to a needle puncture (at the perimeter) but, instead, one would disseminate punctures about the surface of the septum. The life of the septum lasts as long as any one spot in the septum continues to self-seal after being punctured.

There is a direct correlation between the area of a septum to be punctured, and the puncture life of the entire septum. As the area to be repeatedly punctured increases, it is less likely any one spot will experience the repeated puncturing action, and the life of the septum is prolonged. As the area to be repeatedly punctured decreases, it is more likely that any one spot will experience the repeated puncturing action, and the life of the septum is reduced. Thus, the use of a circular ring about the entire perimeter of the septum, causing individuals to repeatedly puncture a limited area of the septum detrimentally, acts to reduce the life of the septum.

Another reason for the need to be sure a septum is accessed (and, thus, the reason individuals will access a septum at its perimeter) has to do with the types of drugs being injected into the implantable device. Sometimes a vesicant drug (one toxic to cellular structures) is injected into an area of the body. Should the vesicant drug be injected about the outside of the housing of the device, instead of through the insertion route defined by the implantable device, necrosis of tissues about the device may occur. Extravasation about the housing results in instability to the implantable device, and possible harm to a patient. One may improperly believe they have accessed the septum if the base of the implantable device is struck by the accessing needle, thus resulting in the dispensation of the vesicant drug to the tissue about the implantable device.

Another problem presented by the use of a raised circular ring is where two septums covering open cavities are implanted in a side-by-side position, but spaced apart somewhat so that two different types of medication may be utilized. In this situation, the doctor has the problem after locating one of the septums, to determine where the second septum is. If the doctor can identify the perimeter of the first septum, the doctor knows that the second septum is positioned somewhere in a circular path around the first septum. However, it becomes necessary to probe around this circular path in order to locate the position of the second septum by virtue of the second raised circular ring. While one might think that locating the second septum would be relatively easy, doctors have experienced some difficulty in this process, particularly when the implantable device has been in position for a long period of time. While a doctor feels about for the septums, the very process of locating the septums impedes access to the septums since the fingers of the doctor are covering one or both of the septums.

Moreover, even if a doctor should identify the location of the first septum and the second septum, a problem still exists. Typically all septums are constructed in a similar fashion. This similarity prevents a doctor from differentiating one septum from another due to the subcutaneous placement of the implantable device. Because multiple septums are generally employed to act as alternate insertion routes to isolate medication and fluids which react with each other, the problem could occur that reactive substances may be placed through the same septum. The potentially harmful circumstances resulting from such an occurrence can be devastating.

An additional problem arises from the fact that the location of structures, separate from the septums, but important nonetheless, cannot be determined due to the subcutaneous placement of the implantable device. Structures, such as the stem of a port, are vital to the continued functioning of a port. It would be a benefit to know their location as well as that of any septums.

Thus, it has become obvious that needed improvements over the prior art would be very desirable, such as a tactile means that more definitively and simultaneously locates the position of each of a plurality of septums, that does not create an enclosed area, that obviates the restriction of access to the septums by the very process of locating the septum, that maximizes the life-span of the septums, which provides some indicating means for locating the stem of a port, and that differentiates between a plurality of septums such that two or more reactive chemicals do not come in contact with each other in the same port chamber to cause a precipitate which could harm a patient.

BRIEF SUMMARY AND OBJECTS OF THE INVENTION

In view of these problems it is a principal object of the present invention to provide an implantable device having tactile means whereby a single tactile indicator simultaneously indicates the position of each of two or more septums.

A second object of the invention is to provide an implantable device having tactile locating means which differentiate between a plurality of septums such that reactive medications or fluids are not delivered to the same open cavity of a septum.

A third object of the invention is to provide an implantable device having tactile locating means which prolong the life of the septums by minimizing the number of punctures to a specific area of the septum.

A fourth object of the invention is to provide an implantable device having a tactile locating means which eliminates, or at least minimizes, the obstruction of access to the septums that is currently caused by the very process of locating the septums.

A fifth object of the invention is to provide an implantable device having tactile locating means which indicate the relative location of the implantable device.

A sixth object of the invention is to provide an implantable device having tactile locating means which indicate the location of the stem of the implantable device.

A seventh object of the present invention is to provide an implantable device having tactile locating means which do not create an enclosed area of tissue or make localized tissue susceptible to necrosis.

In order to accomplish these objectives the implantable device as disclosed herewith has been invented. The invention comprises a housing configured for implantation beneath the skin of a patient having a plurality (usually, but not necessarily, two) open cavities emplaced side by side, and configured so as to contain medicinal or other fluids. Each open cavity is capped by a self-sealing septum.

The housing comprises a cap and a base, configured so as to be fixedly engaged with each other. The cap also secures the septums in position above the open cavities. In the preferred embodiment, having two open cavities a dual-port stem exits the device having two channels, each of which communicates with a respective open cavity; and the stem is configured so as to engage a dual lumen catheter, as is described in more detail below.

The top surface of the cap has a raised locating ridge emplaced thereon, which ridge is positioned so as to be adjacent to, and between, the two septums or other inlet means. The ridge serves as tactile means for a doctor to locate simultaneously the position of both inlet means. The ridge may also comprise indicator means to determine the location of structures comprising the device, such as a stem, or to differentiate between a plurality of septums.

The ridge is preferably configured as a straight line, although other configurations may be preferable for certain applications, or to certain doctors. The straight line ridge is preferably oriented so as to be orthogonal to a line joining the centers of the inlet means. Alternatively, the ridge may be configured so as to be in line with (parallel to) the line joining the centers of the inlet means. In either event, the doctor can tell, once he has located the single ridge, where both inlet means are located. This single ridge feature has been found to be very beneficial and much preferred over existing tactile means.

Other configurations of the ridge are also possible. One such embodiment of the ridge comprises a configuration wherein the ends of the straight line are enlarged. This serves to facilitate locating the ridge. Alternatively, the ridge may be curved rather than straight, such as an "S" curve. Different doctors may prefer these or still different configurations as a matter of choice depending upon the location of the infusing device in the body or the personal preferences of the attending doctors.

In any event, it is an important feature of the present invention that the ridge is configured so as to not enclose an area. There is a fear among many doctors that a raised ridge enclosing an area, as is typical with existing devices, may interfere with the blood flow to the enclosed area, thereby resulting in necrosis of the adjacent tissue. Thus, these doctors prefer a configuration that does not embody this potential danger. Heretofore, the only option has been to avoid the use of a raised tactile surface or to use one that results in necrosis and is not particularly effective in locating the exact position of both inlet means, unlike the present invention.

Existing devices normally employ a self-sealing septum covering the inlet opening to the open cavities. Such septum may be fashioned from a self-sealing polymer such as silicone rubber or latex. The septum is configured such that it may be punctured by a hypodermic needle, catheter, or other means for infusing a fluid and reseal itself after the needle or infusion means has been removed.

As noted above, a stem is connected to the device which comprises two channels communicating respectively with the open cavities. (Of course, if there were three open cavities, the stem would have three channels.) The channels are separately configured, and spaced apart from each other, by an elongated slot for some distance from the distal end of the stem to a point intermediate the length of the stem. Each channel is configured with connecting means. Preferably, each channel is barbed, having an approximately semi-circular raised surface positioned on the outside wall of the channel (or other suitable connector), near the distal end of the stem. The distal face of the raised surface tapers outwardly from the wall of the channel, tapering from its distal end towards its proximal end.

The outside diameter of the raised surface at its maximum position, and the outside diameter of the stem at its proximal end, are substantially the same, and are configured so as to be equal to or slightly larger than the inside diameter of the catheter to be connected thereto. Thus, when the catheter is slid over the stem it expands somewhat and thus snugly engages the stem. The shape of the raised surface serves to prevent it from backing off. As a further securement means a locking sleeve is slid over the engaged catheter and stem, which is sized so as to snugly grip the catheter wall and the stem together.

BRIEF DESCRIPTION OF THE DRAWINGS

Reference is next made to a brief description of the drawings, which are intended to illustrate several different embodiments of the present invention with respect to the manner of making and using same in its presently understood best mode. The drawings and the detailed description which follow are intended to be merely illustrative and not otherwise limiting of the scope of the invention as set forth in the appended claims.

DETAILED DESCRIPTION OF THE ILLUSTRATED EMBODIMENTS

Figure 1:
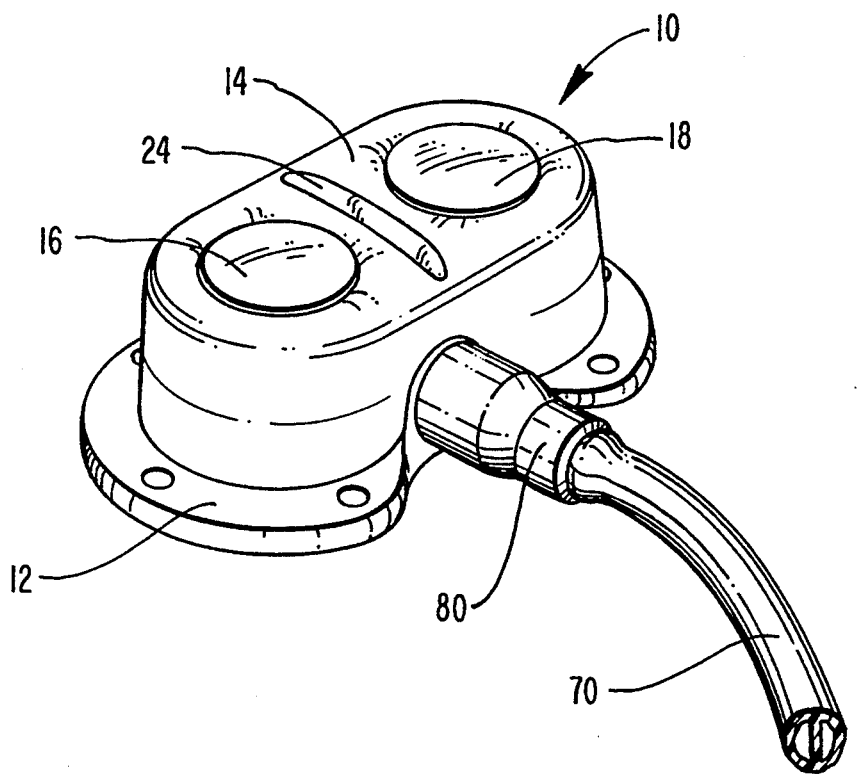
FIG. 1 is a perspective view of the implantable device with the catheter attached.
Figure 2:
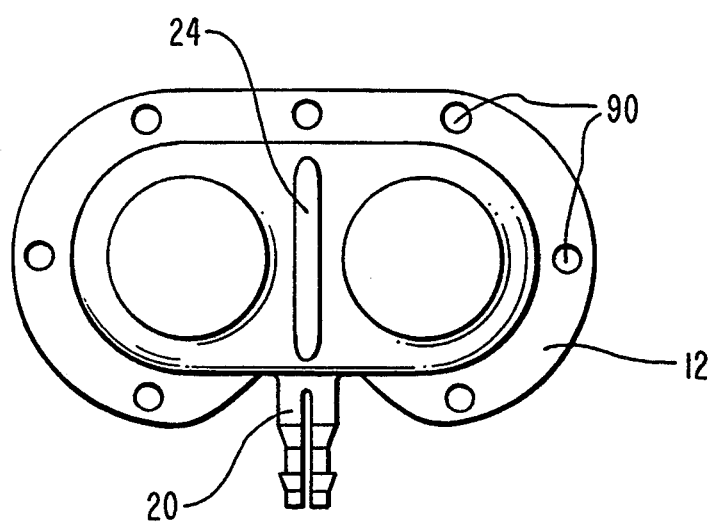
FIG. 2 is a plan view of the device with the catheter removed.
Figure 3:
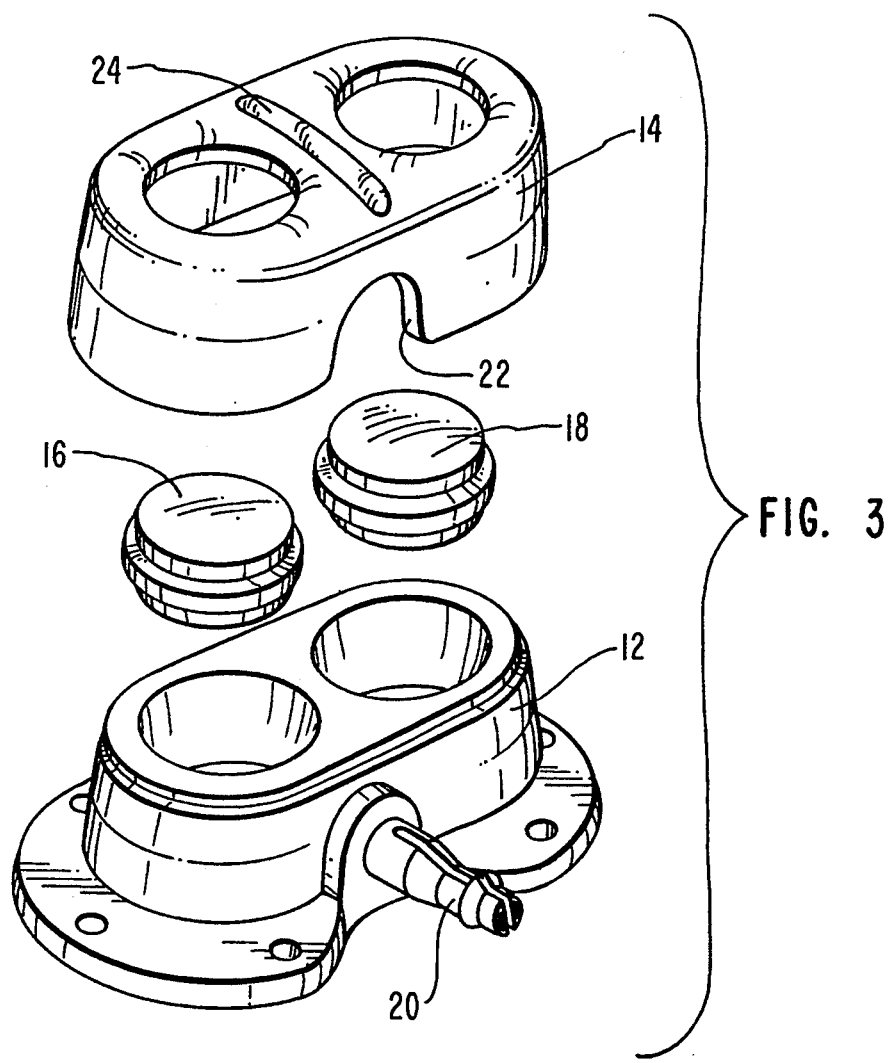
FIG. 3 is an exploded view showing the cap, the base, and two septums.

A perspective view of one embodiment of the implantable device 10 is shown in FIG. 1, a plan view in FIG. 2, and an exploded view in FIG. 3. The device comprises a housing. The housing comprises a base 12, a cap 14, and a plurality of self-sealing septums, preferably two self-sealing septums 16 and 18.

Base 12 and cap 14 are configured so as to be fixedly engaged with each other. Sections 16 and 18 may be fashioned from a self-sealing polymer such as silicone rubber or latex. Septums 16 and 18 are configured such that septums 16 and 18 may be punctured by a hypodermic needle, catheter, or other means for infusing or withdrawing a fluid, and reseal itself after the needle or infusion or withdrawal means has been removed.

The device also comprises a stem 20, to be described in more detail below, is attached to the base 12 and exits from beneath the cap 14 by way of opening 22.

Device 10 further comprises tactile means. As an example not meant to limit the scope of the present invention, a straight-line tactile raised locating ridge 24 is positioned on the top of the cap 14 as shown. Locating ridge 24 is positioned between, and closely adjacent to, septums 16 and 18. Once locating ridge 24 has been found by palpating the skin of the patient, and, it immediately becomes known where both septums 16 and 18 are located. This single ridge feature has been found to be very beneficial and much preferred over existing tactile means.

In this embodiment, the locating ridge 24 is oriented so as to be orthogonal to a line joining the centers of the septums. However, locating ridge 24 could be oriented differently, such as being in line with (parallel to) the line joining the centers of the septums. Various other configurations of locating ridge 24 could be employed, as will be discussed below.

One very important feature of locating ridge 24, as distinguished from prior devices, is the aspect that locating ridge 24 does not encompass an enclosed area. As discussed before, this aspect of locating ridge 24 eliminates the fear of many doctors that a ridge enclosing an area might lead to necrosis. The distinguishing features of locating ridge 24 are that locating ridge 24 is positioned closely adjacent to, and between, the septums, so as to assist the doctor in simultaneously locating the septums by tactile means, and that locating ridge 24 does not enclose an area. Further, once the doctor has located locating ridge 24 he immediately knows where both septums are positioned. It is not necessary for him to locate one septum, and then have to search further for the other one. Still further, through the use of indicator means, comprising the tactile means, to be discussed shortly, a doctor will be able to differentiate between a plurality of septums or to identify the location of structures associated with the septums such as stem 20.

Additionally, and very importantly, the septums can be located by touch without impeding access to the septum, in contrast to prior art devices. This is effected by virtue of the fact that locating ridge 24 is positioned between the septums and does not encircle the septums.

There are many different configurations that the locating ridge 24 might assume and still have the distinguishing features as noted above. Some of these configurations are shown in FIGS. 5, 6, 7, 8, 9, 10 and 11. It should be understood that all such configurations are the subject of this invention, not just those depicted.

Figure 4:
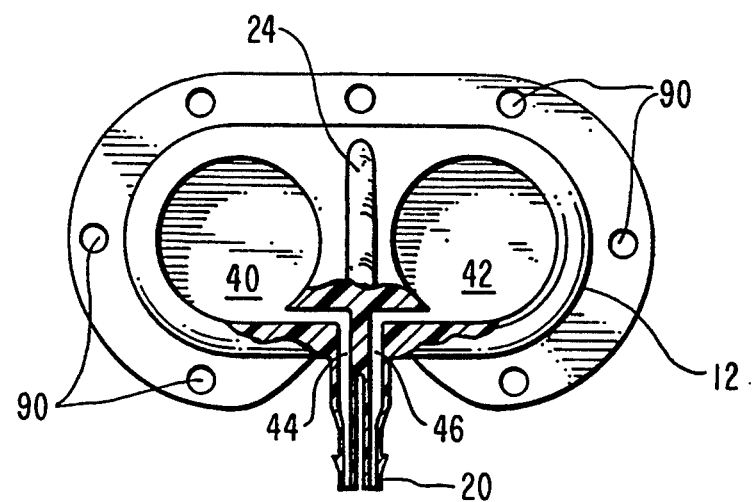
FIG. 4 is a plan view of the base alone.

Positioned beneath septums 16 and 18 are two open cavities 40 and 42, as shown best in FIG. 4. When the septums 16 and 18 and cap 14 are assembled to base 12, open cavities 40 and 42 are sealed. Open cavities 40 and 42 have respective channels 44 and 46 communicating between them and dual-port stem 20.

Figure 12:
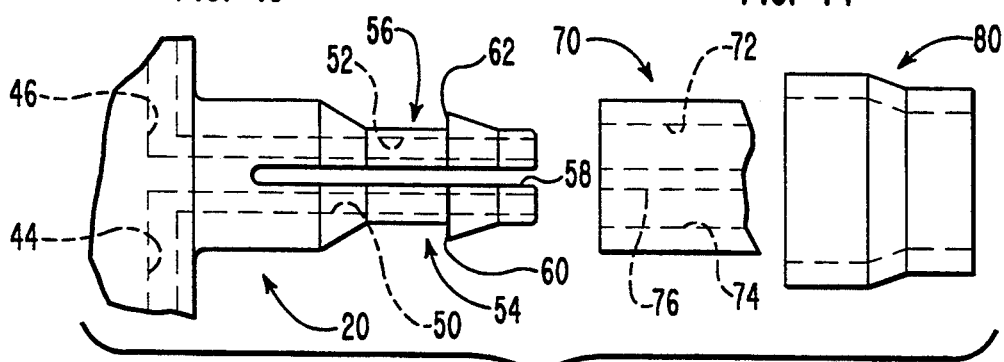
FIG. 12 is an exploded view showing the stem of the device, a portion of the catheter, and the locking sleeve.
Figure 13:
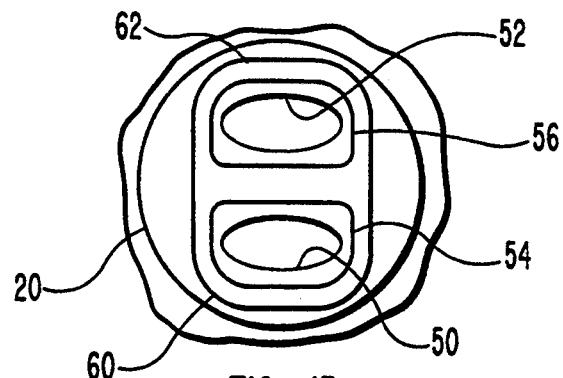
FIG. 13 is an end view of the stem, corresponding to FIG. 12.

Dual-port stem 20 is shown best in FIG. 12. As shown stem 20 has two passageways 50 and 52 which in turn communicate with respective channels 44 and 46. Stem 20 is divided at its distal end into two channels 54 and 56, having a slot 58 separating channels 54 and 56. As shown best in FIG. 13, channels 54 and 56 are substantially rectangular in cross section and have substantially elliptical passageways 50 and 52 passing therethrough. However, these shapes are arbitrary, and may assume other shapes as desired.

Channels 54 and 56 are configured with respective barbs 60 and 62, each of which tapers outwardly from its distal end towards its proximal end, as shown. Barbs 60 and 62 serve as smooth, segmental perimeters which tend to frictionally engage and lock a catheter slid over stem 20, as described more fully below. The maximum diameter of the raised surface is substantially the same as the maximum diameter of stem 20 at its proximal end, as depicted.

As shown best in FIG. 12, the catheter 70 is a dual lumen catheter having semi-elliptical lumens 72 and 74 passing therethrough, separated from each other by a web 76 which is sized so as to engage slot 58 when catheter 70 is slid over stem 20. The internal diameter of catheter 70 is approximately equal to, or slightly less than, the maximum diameter of stem 20 and the raised surfaces on barbs 60 and 62. Thus, as catheter 70 is slid over stem 20, it expands slightly, thereby ensuring a snug fit. Catheter 70 is preferably fashioned from a resilient polymer, such as silicone.

A locking sleeve 80 also serves to lock catheter 70 to stem 20. Locking sleeve 80 is configured so as to slide over catheter 70 following assembly of catheter 70 to stem 20, thereby pressing the wall of catheter 70 tightly against the outer wall of stem 20 and barbs 60 and 62—actually compressing the wall between locking sleeve 80 and stem 20 at a position intermediate thereupon. Thus, a secure attachment is effected, without the necessity of rotating any components.

Figure 5:
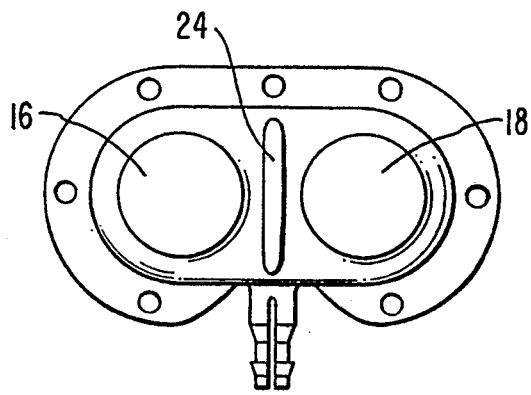
FIG. 5 is a schematic view of the top face of the cap showing a preferred straight-line embodiment of the raised locating ridge.

As noted above, various configurations of locating ridge 24 may be employed. FIG. 5 is a schematic view of the top face of cap 14 showing the preferred straight-line embodiment of locating ridge 24. The longitudinal location of locating ridge 24 allows one to determine the position of septums 16 and 18. If a doctor is aware that septums 16 and 18 are located along the side of locating ridge 24, longitudinally oriented as in FIG. 5, the doctor will be able to employ the tactile means for locating simultaneously the position of both septums 16 and 18.

Figure 6:
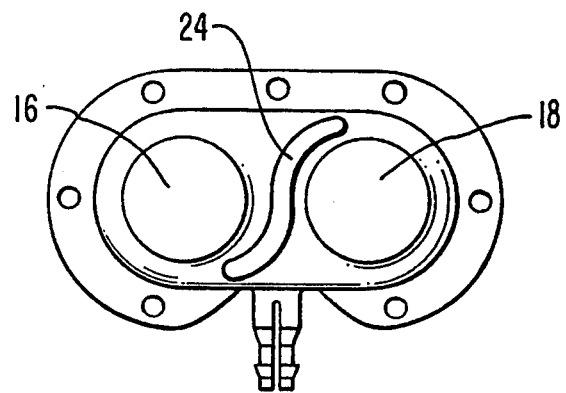
FIG. 6 corresponds to FIG. 5 except that the locating ridge is "S" shaped.
Figure 7:
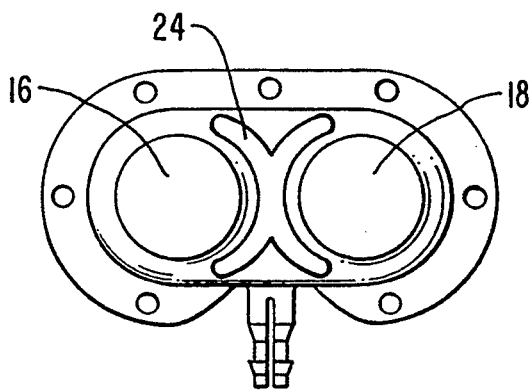
FIG. 7 corresponds to FIG. 5 except that the locating ridge is "X"-shaped.
Figure 8:
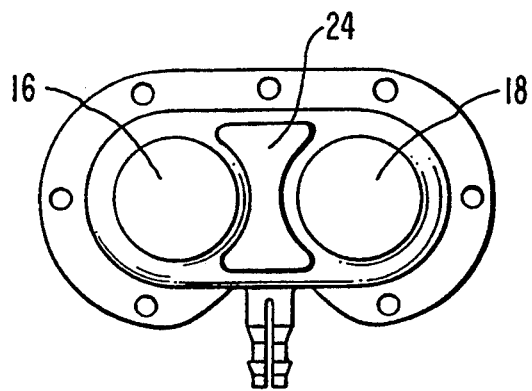
FIG. 8 corresponds to FIG. 5 except that the locating ridge is enlarged at both ends.
Figure 9:
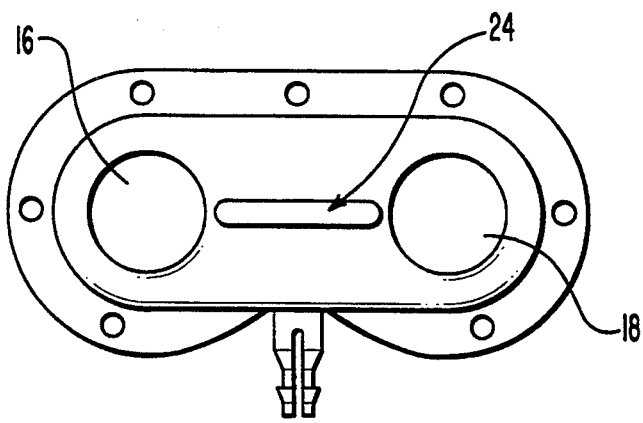
FIG. 9 corresponds to FIG. 5 except that the locating ridge is laterally positioned between the septums.

FIGS. 6–9 provide for tactile means which are similar to the tactile means employed in FIG. 5, however, certain differences exist. Each locating ridge 24 outlines to some degree the configuration of the septum positioned next to locating ridge 24. In each of the embodiments displayed, either one or both, or some portion of septums 16 and 18 are outlined by locating ridge 24 in an attempt to more clearly distinguish septums 16 and 18. As an example, FIG. 6 depicts locating ridge 24 having an "S" shape. FIG. 8 depicts locating ridge 24 similar to FIG. 5, but having enlarged ends. FIG. 9 depicts a straight-line locating ridge 24 in line with the line joining the centers of septums 16 and 18. It is important to note, however, that septums 16 and 18 are not completely enclosed by locating ridge 24, since this could result in necrosis of the tissues associated within locating ridge 24.

Figure 10:
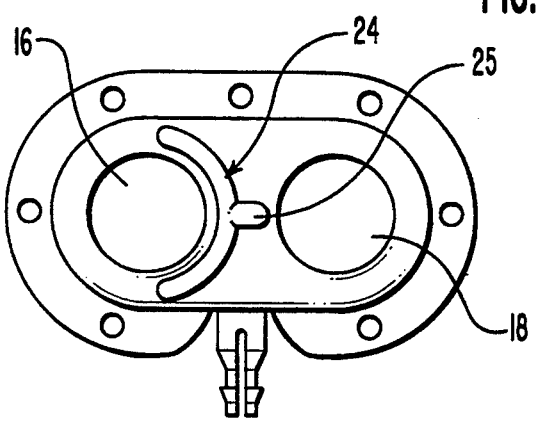
FIG. 10 corresponds to FIG. 5 except that the locating ridge is arrow-shaped at one end pointing in the direction of the locking sleeve.
Figure 11:
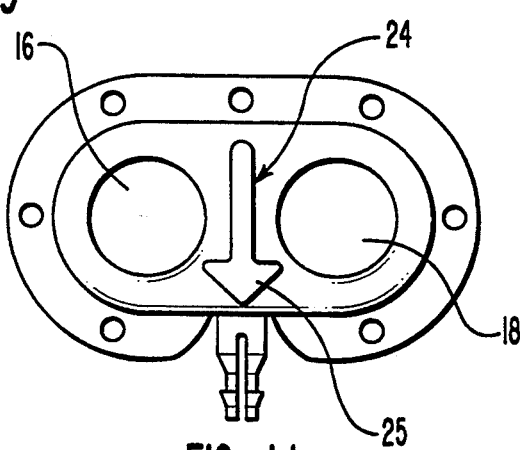
FIG. 11 corresponds to FIG. 5 except that the locating ridge is curved and has an appendage pointing towards one of the septums.

In FIGS. 10 and 11, locating ridge 24 further comprises indicating means. As indicated in each drawing, the generally longitudinal length of tactile locating ridge 24 is provided with an appendage 25. Appendage 25 may extend in a direction contrary to the direction indicated by the long locating ridge 24; appendage 25 may even take the form of an arrow-shape. Use of appendage 25, in relation to the general direction provided by locating ridge 24, may further indicate some area of interest to a physician.

For example, in FIG. 10 locating ridge 24 is placed between septums 16 and 18. Were one to seek to identify or differentiate septums 16 and 18 while the implantable was subcutaneously placed, one would discover this was impossible. The use of appendage 25, however, pointing directly at septum 18, allows one to differentiate septums 16 and 18. If a doctor is previously aware of the fact that septum 18 and appendage 25 are located to the right of locating ridge 24, the physician could, through tactile sensation of locating ridge 24 and appendage 25, sense where septum 18 lies in relation to septum 16.

In FIG. 11, appendage 25 is used to indicate to a physician where the stem of the port is located. By placing appendage 25 at the end of a straight locating ridge 24 lying in the same plane as the stem, a physician will know whether or not the stem is located at one end or the other of locating ridge 24.

It should also be mentioned that indicator means, such as appendage 25, may not be necessary to enable a doctor to differentiate between a pair of septums. Tactile locating means can, by their sole use, be used to differentiate between a pair of septums by virtue of its configuration. As an example, which is not meant to limit the present invention, locating ridge 24 could be a semi-circular segment enclosing only a portion of one of two septums. If a doctor is previously aware of which septum is partially enclosed by locating ridge 24, the two septums can be differentiated. Locating ridge 25 may be placed between septums 16 and 18, and partially encircle septum 16 and not septum 18, as illustrated in FIG. 10 if appendage 25 were not shown.

Referring once again to base 12 as shown in FIG. 4, a number of openings 90 are fashioned in the flange of base 12. These are used to allow the doctor to suture the implantation device to tissues under the skin of the patient, in a manner well known and not further described herein.

By way of example, and not to be considered at all as limiting, the overall dimensions of the device are preferably approximately 1.75 inches by 1 inch. The maximum diameter of stem 20 is approximately 3/16 inch. Raised locating ridge 24 is approximately 1/16 inch high. It will be appreciated that these dimensions may vary depending upon the size of the open cavity necessary for the medicinal fluids.

In use, device 20 and catheter 70 are implanted beneath the skin of a patient. Generally, device 10 is placed in the chest wall (infraclavicular space) on either the right or left side supported by the underlying ribs. A pocket incision is made about the size of the length of the diameter of base 12. Preferably, device 10 is buried only about one-half (0.5) inch below the skin, which is generally sufficient to prevent device 10 from eroding through the skin. Four nonabsorbable sutures are used to anchor device 10 to the underlying fascia using suture stabilization points of base 12.

Catheter 10 may be inserted so that the distal end of catheter 70 is placed in the superior vena cava and the body of catheter 70 lies freely in that vessel. After catheter 70 is thusly positioned, sufficient slack to allow for normal body movement without straining catheter 70 is left in the point of entry of catheter 70 into the vascular system and device 10. The free end of catheter 70 is then tunneled from its point of entry into the vascular system to the pocket.

An initial supply of medicament is then injected into an insertion route through open cavities 40 and 42. When the medicament is substantially all dispensed, the doctor will typically flush the insertion route to conclude a bolus infusion. To introduce the medicament, the doctor must first locate septums 16 and 18. This is achieved by tactile means, such as by feeling with the fingers. When locating ridge 24 under the skin is discovered in this manner, immediately the location of both septums 16 and 18 becomes known, these being on either side of locating ridge 24. The doctor also can differentiate between septums 16 and 18 if some indicating means is provided to locate a certain septum. With the arrangement of the invention he can accomplish the foregoing without the necessity of removing his finger from locating ridge 24, or blocking the entrance to either septum 16 or 18. This has proven to be of significant advantage.

In summary, the single tactile locating ridge 24 enables the doctor to locate both septums 16 and 18 simultaneously. The placement of locating ridge 24, being between septums 16 and 18 rather than encircling septums 16 and 18, fulfills the objective of the doctor being able to inject medication into open cavities 40 and 42 without the fingers of the doctor obstructing septums 16 and 18. Additionally, the configuration of tactile locating ridge 24 is such that no enclosed area of skin is created by locating ridge 24, thus dispensing with the fear of necrosis. Further, indicating means are provided to differentiate between septums 16 and 18, or to locate stem 20 of the device. Finally, the locating means results in a fewer number of insertions through a specific area of septums 16 and 18 being necessary, thus prolonging the life of the device.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An implantable device capable of embedment beneath the skin of a patient, the device enabling repeated, non-destructive fluid communication of the distal end of a tubular member, such as a needle or a catheter, piercing the skin of the patient with the proximal end of a selected one of the lumens of a multi-lumen catheter, said device comprising:

a. a housing enclosing a first fluid cavity and a second fluid cavity, said housing defining a first access aperture communicating through said housing with said first fluid cavity and a second access aperture communicating through said housing with said second fluid cavity;

b. first self-sealing means for sealing said first access aperture and for admitting the distal end of the tubular member into said first fluid cavity, thereby to enable the infusion of fluids thereinto through the tubular member;

c. second self-sealing means for sealing said second access aperture and for admitting the distal end of the tubular member into said second fluid cavity, thereby to enable the infusion of fluids thereinto through the tubular member;

d. means for communicating fluid from each of said first fluid cavity and said second fluid cavity to the patient through a respective one of the lumens of the multi-lumen catheter; and e. tactile means positioned between the first and the second self-sealing means for simultaneously locating the positions of both of said first and said second self-sealing means by palpating the skin of the patient without thereby impeding access by the distal end of the tubular member to either of said first or said second self-sealing means during palpation of said tactile means, the tactile means comprising a raised locating ridge on the surface of the housing, the locating ridge being configured so as to avoid encircling tissue of the patient that contacts said surface of said housing, and said locating ridge being substantially straight and being so disposed on said surface of said housing as to traverse and be oriented substantially orthogonally to a line connecting the centers of said first and said second self-sealing means.

2. An implantable device as defined in claim 1, wherein said first self-sealing means comprises a first needle-penetrable septum, and said second self-sealing means comprises a second needle-penetrable septum.

3. An implantable device as defined in claim 1, further comprising means for locking the catheter to the implantable device.

4. An implantable device capable of embedment beneath the skin of a patient, the device enabling repeated, non-destructive fluid communication of the distal end of a needle piercing the skin of the patient with the proximal end of a selected one of the lumens of a dual-lumen catheter, said device comprising:
  a. a housing enclosing a first fluid cavity and a second fluid cavity, said housing defining in a top surface thereof a first access aperture communicating through said housing with said first fluid cavity and a second access aperture communicating through said housing with said second fluid cavity;
  b. a first needle-penetrable septum sealing said first access aperture;
  c. a second needle-penetrable septum sealing said second access aperture, the line connecting the center of said first septum and the center of said second septum defining a longitudinal axis of said top surface of said housing;
  d. means for communicating fluid from each of said first fluid cavity and said second fluid cavity to a respective one of the lumens of the dual-lumen catheter; and
  e. a locating ridge on said top surface of the housing, said locating ridge being raised relative to said top surface of said housing and terminating at each extreme thereof in first and second ends whereat said locating ridge ceases to be raised relative to said top surface of said housing, said locating ridge traversing said longitudinal axis of said top surface between said first septum and said second septum and being disposed with said first and second ends thereof entirely interior of a tactile ridge locating region on said top surface of said housing, said tactile ridge locating region being limited in a direction parallel to said longitudinal axis of said top surface to a region between a first linear boundary and a second linear boundary, said first linear boundary passing through said center of said first septum perpendicular to said longitudinal axis of said top surface, and said second linear boundary passing through said center of said second septum perpendicular to said longitudinal axis of said top surface.

5. An implantable device as defined in claim 4, wherein said means for communicating comprises an outlet stem having a proximal end and a distal end, the proximal end of said outlet stem being attached to the housing and having two separate enclosed stem channels, each of said stem channels communicating with a respective one of said first and said second fluid reservoirs and being longitudinally formed through an individual one of a pair of separately configured prongs, said prongs being spaced apart from each other by an elongate slot extending from the distal end of said outlet stem to a point intermediate the length of said outlet stem, the proximal end of said outlet stem being configured so as to snugly and slidably accept the dual-lumen catheter with each lumen of the catheter communicating with a respective one of the stem channels.

6. An implantable device as defined in claim 5, wherein said means for communicating further comprises a locking sleeve capable of slidably engaging the exterior of the dual-lumen catheter after the catheter has been accepted on said outlet stem, the locking sleeve being so configured as to compress the wall of the catheter against the outer wall of said outlet stem at a position intermediate thereupon, thereby to lock the catheter to said outlet stem.

7. An implantable device as defined in claim 5 further comprising a dual-lumen catheter wherein a web separates the lumens of the dual-lumen catheter, and the web is received into said slot between said prongs of said outlet stem when the catheter is accepted on said outlet stem.

8. An implantable device as defined in claim 5, wherein the locating ridge comprises indicator means determine the location of the outlet stem in relation to the first and second septums.

9. An implantable device as defined in claim 8, wherein the indicator means comprises an arrow-shaped appendage.

10. An implantable device as defined in claim 4, wherein the locating ridge is substantially straight.

11. An implantable device as defined in claim 10, wherein the locating ridge is is oriented substantially orthogonally to said longitudinal axis of said top surface of said housing.

12. An implantable device as recited in claim 11, wherein said locating ridge is enlarged at one end thereof.

13. An implantable device as defined in claim 4, wherein the housing comprises a cap and base in fixed engagement with each other.

14. An implantable device as defined in claim 13, wherein the housing is comprised of plastic.

15. An implantable device as defined in claim 13, wherein the cap comprises an upper wall having a top surface and an encircling skirt depending from the periphery of said upper wall.

16. An implantable device as defined in claim 15, wherein the locating ridge is integrally formed on the top surface of the cap of said housing.

17. An implantable device as defined in claim 15, wherein the encircling skirt is configured with an opening therethrough sized and shaped so as to permit the passage therethrough of said means for communicating when the cap and the base are fixedly engaged with each other.

18. An implantable device as defined in claim 13, wherein the base comprises a floor having a flat bottom surface, and on the side of said floor opposite from said bottom surface said base is formed into two recesses configured so as to comprise respectively said first and second cavities.

19. An implantable device as defined in claim 4, wherein the locating ridge is substantially straight and is oriented substantially parallel to a line connecting the centers of the first and second self-sealing means.

20. An implantable device as defined in claim 4, wherein the locating ridge comprises an elongate shape, each end of said elongate shape being enlarged with respect to a portion intermediate the ends thereof.

21. An implantable device as defined in claim 4, wherein the locating ridge is substantially "S"-shaped.

22. An implantable device as defined in claim 4, wherein the locating ridge is substantially "X"-shaped.

23. An implantable device as defined in claim 4, wherein the locating ridge comprises:
  a. a circular segment; and
  b. a short straight line segment oriented substantially parallel to a line connecting the centers of the first and second septums.

24. An implantable device as defined in claim 4, wherein the locating ridge comprises indicator means to differentiate between said first and second septums.

25. An implantable device capable of embedment beneath the skin of a patient, the device enabling repeated nondestructive fluid communication by the distal end of a needle piercing the skin of the patient with a selected one of a first fluid cavity or a second fluid cavity formed in the device, said device comprising:
  a. a housing enclosing the first fluid cavity and the second fluid cavity, said housing defining a first access aperture communicating through said housing with said first fluid cavity and a second access aperture communicating through said housing with said second fluid cavity;
  b. a first needle-penetrable septum sealing said first access aperture;
  c. a second needle-penetrable septum sealing said second access aperture; and
  d. a raised locating ridge integrally formed on the surface of said housing between said first septum and said second septum, said locating ridge being configured so as to avoid encircling tissue of the patient contacting the surface of said housing when said device is embedded beneath the skin of the patient, said locating ridge being substantially straight and being so disposed on said surface of said housing as to traverse and be oriented substantially orthogonally to a line connecting the center of said first septum and the center of said second septum.

26. An implantable device as recited in claim 25, further comprising an outlet stem having a proximal end and a distal end, said proximal end of said outlet stem being attached to said housing and having two separate enclosed stem channels, each of said stem channels communicating with a respecting one of said first and said second fluid reservoirs and being longitudinally formed through an individual one of a pair of separately configured prongs, said prongs being spaced apart from each by an elongate slot extending from the distal end of said outlet stem to a point intermediate the length of said outlet stem, said proximal end of said outlet stem being configured so as to snugly and slidingly accept the dual-lumen catheter with each lumen of the catheter communicating with a respective stem passageway of said outlet stem, and with a web of the catheter that separates the lumens thereof being received into said slot between said prongs of said outlet stem.

27. An implantable device capable of embedment beneath the skin of a patient, the device enabling repeated, non-destructive fluid communication by the distal end of a tubular member, such as a needle or a catheter, piercing the skin of the patient with a selected one of a first fluid cavity or a second fluid cavity formed in the device, said device comprising:
  a. a housing enclosing the first fluid cavity and the second fluid cavity, said housing defining a first access aperture communicating through said housing with the first fluid cavity and a second access aperture communicating through said housing with the second fluid cavity;
  b. first self-sealing means for sealing said first access aperture and for admitting the distal end of the tubular member into the first fluid cavity, thereby to enable the infusion of fluids thereinto through the tubular member;
  c. second self-sealing means for sealing said second access aperture and for admitting the distal end of the tubular member into the second fluid cavity, thereby to enable the infusion of fluids thereinto through the tubular member;
  d. a substantially straight tactile locating ridge upstanding on the surface of said housing between said first self-sealing means and said second self-sealing means, said locating ridge being so disposed on said surface of said housing as to traverse and be oriented substantially orthogonally to a line connecting the center of said first self-sealing means and the center of said second self-sealing means.

28. An implantable device as recited in claim 27, wherein said locating ridge is enlarged at one end thereof.

29. An implantable device capable of embedment beneath the skin of a patient, the device enabling repeated, non-destructive fluid communication of the distal end of a tubular member, such as a needle or a catheter, piercing the skin of the patient with the proximal end of a selected one of the lumens of a multi-lumen catheter, said device comprising:
  a. a housing enclosing a first fluid cavity and a second fluid cavity, said housing defining in a top surface thereof a first access aperture communicating through said housing with said first fluid cavity and a second access aperture communicating through said housing with said second fluid cavity;
  b. first self-sealing means for sealing said first access aperture and for admitting the distal end of the tubular member into said first fluid cavity, thereby to enable the infusion of fluids thereinto through the tubular member;
  c. second self-sealing means for sealing said second access aperture and for admitting the distal end of the tubular member into said second fluid cavity, thereby to enable the infusion of fluids thereinto through the tubular member, the line connecting the center of said first self-sealing means and the center of said second self-sealing means defining a longitudinal axis of said top surface of said housing;
  d. means for communicating fluid from each of said first fluid cavity and said second fluid cavity to the patient through a respective one of the lumens of the multi-lumen catheter; and
  e. a locating ridge on said top surface of the housing, said locating ridge being raised relative to said top surface of said housing and terminating at each extreme thereof in first and second ends whereat said locating ridge ceases to be raised relative to said top surface of said housing, said locating ridge traversing said longitudinal axis thereof between said first self-sealing means and said second self-sealing means and being with said first and second ends thereof disposed entirely interior of a tactile ridge locating region on said top surface of said housing, said tactile ridge locating region being limited in a direction parallel to said longitudinal axis of said top surface to a region between a first linear boundary and a second linear boundary, said first linear boundary passing through said center of said first self-sealing means perpendicular to said longitudinal axis of said top surface, and said second linear boundary passing through said center of said second self-sealing means perpendicular to said longitudinal axis of said top surface.

30. An implantable device as recited in claim 29, wherein said tactile locating ridge is substantially straight and is oriented substantially orthogonally to said longitudinal axis of said top surface of said housing.

31. An implantable device as defined in claim 29, wherein the locating ridge is substantially straight and is oriented substantially parallel to a line connecting the centers of the first and second self-sealing means.

32. An implantable device as defined in claim 29, wherein the locating ridge comprises an elongate shape, each end of said elongate shape being enlarged with respect to a portion intermediate the ends thereof.

33. An implantable device as defined in claim 29, wherein the locating ridge is substantially "S" shaped.

34. An implantable device as defined in claim 29, wherein the locating ridge is substantially "X"-shaped.

35. An implantable device as defined in claim 29, wherein the locating ridge comprises:

a. a circular segment; and b. a short straight line segment oriented substantially parallel to a line connecting the first and second centers of the self-sealing means.

36. An implantable device as defined in claim 29, wherein the tactile means comprises indicator means to differentiate between said first and said second self-sealing means.

37. An implantable device as defined in claim 29, wherein the tactile means comprises indicator means to determine the location of said means for communicating fluid in relation to the first and the second self-sealing means.

38. An implantable device as defined in claim 37, wherein the indicator means comprises an arrow-shaped appendage.

* * * * *

UNITED STATES PATENT AND TRADEMARK OFFICE
CERTIFICATE OF CORRECTION

PATENT NO. : 5,360,407
DATED : November 1, 1994
INVENTOR(S) : ARNOLD S. LEONARD et al.

It is certified that error appears in the above-indentified patent and that said Letters Patent is hereby corrected as shown below:

```
On the Title Page, under item [19], insert --et al.-- after "Leonard"
and item [75], change "Arnie" to --Arnold S.--

Title page, line 2, "Leonard" should be --Leonard et al.--
Column 6, line 48, delete "and,"
Column 12, line 6, before "determine" insert --to--
Column 13, line 22, "orthogonally" should be --orthogonal--
Column 16, line 5, "tactile means" should be --locating ridge--
Column 16, line 9, "tactile means"  should be --locating ridge--
Title page, item [75], "Arnie Leonard" should be
```
--Arnold S. Leonard--

Signed and Sealed this

Thirteenth Day of June, 1995

*Attest:*

BRUCE LEHMAN

*Attesting Officer*  *Commissioner of Patents and Trademarks*